(12) United States Patent
Mizutani

(10) Patent No.: US 8,759,078 B2
(45) Date of Patent: Jun. 24, 2014

(54) BIOCHEMICAL REACTION CASSETTE AND DETECTION APPARATUS FOR BIOCHEMICAL REACTION CASSETTE

(75) Inventor: Yuri Mizutani, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 811 days.

(21) Appl. No.: 12/728,114

(22) Filed: Mar. 19, 2010

(65) Prior Publication Data

US 2010/0267579 A1    Oct. 21, 2010

Related U.S. Application Data

(62) Division of application No. 11/603,832, filed on Nov. 24, 2006, now abandoned.

(30) Foreign Application Priority Data

Nov. 29, 2005   (JP) .................................. 2005-344368

(51) Int. Cl.
*C12M 1/34* (2006.01)
*B01L 3/00* (2006.01)

(52) U.S. Cl.
CPC .......... *C12M 1/34* (2013.01); *B01J 2219/00497* (2013.01); *B01L 3/5025* (2013.01)
USPC ..................................................... 435/287.2

(58) Field of Classification Search
None
See application file for complete search history.

(56) References Cited

U.S. PATENT DOCUMENTS

| 5,585,275 A * | 12/1996 | Hudson et al. ................ 436/518 |
| 7,294,478 B1 * | 11/2007 | Hinchcliffe ..................... 435/7.9 |
| 2003/0032191 A1 * | 2/2003 | Hilson et al. ..................... 436/47 |
| 2005/0089208 A1 * | 4/2005 | Dong et al. .................... 382/133 |
| 2007/0003958 A1 | 1/2007 | Okamoto et al. |
| 2007/0122899 A1 | 5/2007 | Mizutani |

FOREIGN PATENT DOCUMENTS

| JP | 10-505410 | 5/1998 |
| WO | 95/33846 | 12/1995 |

* cited by examiner

*Primary Examiner* — Chris L Chin
*Assistant Examiner* — Richard Moerschell
(74) *Attorney, Agent, or Firm* — Fitzpatrick, Cella, Harper and Scinto

(57) ABSTRACT

A biochemical reaction cassette comprises: a substrate carrying probes immobilized thereon, the probes being adapted to be specifically bound to a target substance; a reaction space forming member for forming a reaction space with the substrate; an elastic member; and an anchor member for supporting the substrate so as to keep it movable relative to the reaction space forming member by way of the elastic member.

3 Claims, 5 Drawing Sheets

BIOCHEMICAL REACTION CASSETTE AND DETECTION APPARATUS FOR BIOCHEMICAL REACTION CASSETTE

This application is a divisional of application Ser. No. 11/603,832, filed Nov. 24, 2006, the contents of which are incorporated herein by reference.

BACKGROUND OF THE INVENTION

1. Field of the Invention

The present invention relates to a biochemical reaction cassette, a detection apparatus to be used for such a biochemical reaction cassette and a detection method for detecting a target substance caught by the probes of such a biochemical reaction cassette.

2. Description of the Related Art

Currently, massive research efforts are being paid in a short period of time to look into the polymorphism and the expression amount of genes in conjunction with the progress of the technology of analyzing genomic information. DNA micro-arrays are being popularly used as means for analyzing genomic information under the circumstances where genomic information is required to be analyzed with such a high degree of throughput. A DNA micro-array is prepared by highly densely immobilizing a large number of probes that can specifically be bound to a biomolecule such as DNA on a substrate such as a glass slide. Genes are extracted from a specimen such as blood taken from a subject, then amplified and labeled typically by a fluorescent dye. As the labeled genes are developed on a DNA micro-array by an appropriate means and the reaction conditions including the temperature are adjusted, a hybridization reaction takes place between the developed genes and the probes. When the specimen contains genes that can specifically be bound to the probes, they are bound to the corresponding probes. Since the genes are labeled in advance, it is possible to determine the type and the quantity of the genes contained in the specimen from the positions on the DNA micro-array where the labels emit a signal and the intensity of the signal.

Known specimen analyzing apparatus adapted to use a DNA micro-array include those for extracting genes from a specimen, those for amplifying the extracted genes and those for labeling genes with a fluorescent dye as well as those for developing the genes labeled by means of any of above listed apparatus and causing a hybridization reaction to take place and those for detecting the positions of fluorescent labels and the intensities of fluorescence on the DNA micro-array after the reaction. However, the operation of any of such apparatus is time consuming and cumbersome because the genes extracted from the specimen have to be moved from apparatus to apparatus by hand. Additionally, a huge space is required to install all such apparatus. Currently, such specimen analyzing apparatus are mostly for research applications. In other words, the time-consuming and cumbersome operation and the requirement for a large space may not raise a particular problem for the present. However, as the performance of DNA micro-arrays is improved in the near future, specimen analyzing apparatus of the type under consideration will find applications in the field of clinical practice for the purpose of examinations. Then, the time-consuming and cumbersome operation and the requirement for a large space will constitute a barrier against quick examinations.

A compact biochemical reaction cassette realized by integrally combining such apparatus other than a fluorescence detection apparatus has been developed to dissolve the problem of cumbersomeness operation and the requirement for a large space (Japanese Patent Application Laid-Open No. H10-505410). The DNA micro-array that is arranged in such a biochemical reaction cassette is downsized as compared with the micro-arrays arranged in known apparatus. To accurately detect signals of fluorescence by means of such a downsized DNA micro-array, the DNA micro-array has to be arranged in parallel with the detection surface of the detection apparatus and secured there. Then, a highly precise adjustment mechanism is required to accurately place the DNA micro-array in position. Additionally, in the analysis of genomic information that utilizes a specific binding of DNA, a denaturing process (of heating to a temperature level higher than the melting temperature Tm) for the purpose of reducing a double-stranded DNA to a single-stranded DNA and/or a hybridization reaction or some other reaction that needs to be conducted at high temperature are often required. Then, the biochemical reaction cassette itself can be deformed by heat applied to it. Thus, even if the DNA micro-array is successfully arranged in parallel with the detection surface of the detection apparatus and secured there initially, the plane of the DNA micro-array may not be kept in parallel with the detection surface of the detection apparatus. In such a case, it may not be able to accurately define the focal point of the detection apparatus. The net result will be that the operation of detecting signals of fluorescence may not reliably be conducted.

In view of the above-identified circumstances, it is therefore an object of the present invention to provide a method of using a biochemical reaction cassette comprising a DNA micro-array and keeping the plane of the DNA micro-array in parallel with the detection surface of a detection apparatus in order to make it possible to accurately detect a desired target substance such as genes by way of a simple operation. Another object of the present invention is to provide a biochemical reaction cassette and a detection apparatus to be used for such a biochemical reaction cassette to which the method of the present invention is applicable.

It may be needless to say that the scope of application of the present invention is by no means limited to DNA micro-arrays and the present invention can be applied to probe arrays where biomolecules of any of various types are arranged on a substrate as probes.

SUMMARY OF THE INVENTION

According to an aspect of the present invention, there is provided a biochemical reaction cassette comprising: a substrate carrying probes immobilized thereon, the probes being adapted to be specifically bound to a target substance; a reaction space forming member for forming a reaction space with the substrate; an elastic member; and an anchor member for supporting the substrate so as to keep it movable relative to the reaction space forming member by way of the elastic member.

In another aspect of the present invention, there is provided a detection apparatus provided with a biochemical reaction cassette for detecting a target substance caught by probes, the apparatus comprising: the biochemical reaction cassette including: a substrate carrying probes immobilized thereon, the probes being adapted to be specifically bound to the target substance; a reaction space forming member for forming a reaction space with the substrate; an elastic member; and an anchor member for supporting the substrate so as to keep it movable relative to the reaction space forming member by way of the elastic member; a detector having a detection surface for detecting the target substance caught by the probes of the biochemical reaction cassette; three or more than three supports having respective front end sections; a mechanism for contacting the supports to the substrate; and a holding structure for holding the biochemical reaction cassette; wherein the plane including the front end sections of the three or more than three supports is parallel to the detection surface.

In still another aspect of the present invention, there is provided a detection apparatus provided with a biochemical reaction cassette for detecting a target substance caught by probes, the apparatus comprising: a biochemical reaction cassette including: a substrate carrying probes immobilized thereon, the probes being adapted to be specifically bound to the target substance; and a reaction space forming member for forming a reaction space with the substrate; a detector having a detection surface for detecting the target substance caught by the probes of the biochemical reaction cassette; three or more than three supports having respective front end sections; a mechanism for contacting the supports to the substrate; a holding structure for holding the biochemical reaction cassette; and an elastic member for supporting the biochemical reaction cassette so as to be movable relative to the holding structure; wherein the biochemical reaction cassette is anchored to the holding structure by way of the elastic member; and the plane including the front end sections of the three or more than three supports is parallel to the detection surface.

In still another aspect of the present invention, there is provided a method of detecting a target substance caught by probes of a biochemical reaction cassette, the method comprising steps of: supporting the biochemical reaction cassette by means of a holding structure; the biochemical reaction cassette including: a substrate carrying probes immobilized thereon, the probes being adapted to be specifically bound to a target substance; a reaction space forming member for forming a reaction space with the substrate; an elastic member; and an anchor member for supporting the substrate so as to keep it movable relative to the reaction space forming member by way of the elastic member; correcting a posture of the substrate relative to the reaction space forming member, while pressing three or more than three supports having respective front end sections against the substrate and elastically deforming the elastic member; and detecting the target substance caught by the probes of the substrate by a detection means having a detection surface; wherein the plane including the front end sections of the three or more than three supports is parallel to the detection surface.

In a further aspect of the present invention, there is provided a method of detecting a target substance caught by probes of a biochemical reaction cassette, the method comprising steps of: supporting the biochemical reaction cassette by means of a holding structure by way of an elastic member; the biochemical reaction cassette including: a substrate carrying probes immobilized thereon, the probes being adapted to be specifically bound to a target substance; a reaction space forming member for forming a reaction space with the substrate; and an anchor member for supporting the substrate so as to keep it movable relative to the reaction space forming member by way of the elastic member; correcting a posture of the substrate relative to the reaction space forming member, while pressing three or more than three supports having respective front end sections against the substrate and elastically deforming the elastic member; and detecting the target substance caught by the probes of the substrate by a detection means having a detection surface; wherein the plane including the front end sections of the three or more than three supports is parallel to the detection surface.

Thus, according to the present invention, when mounting a biochemical reaction cassette in a detection apparatus, it is possible to correct with ease the posture of the substrate arranged in the biochemical reaction cassette so as to make it run in parallel with the detection surface of the detection apparatus and hold it in position if the substrate is initially not highly accurately held in parallel. Then, as a result the detection accuracy is improved to make it possible to highly accurately detect the target substance.

Other features of the present invention will become apparent from the following description of exemplary embodiments with reference to the attached drawings, in which like reference characters designate the same or similar parts throughout the figures thereof.

DESCRIPTION OF THE EMBODIMENTS

Preferred embodiments of the present invention will now be described in detail in accordance with the accompanying drawings.

1st Embodiment

Figure 1:
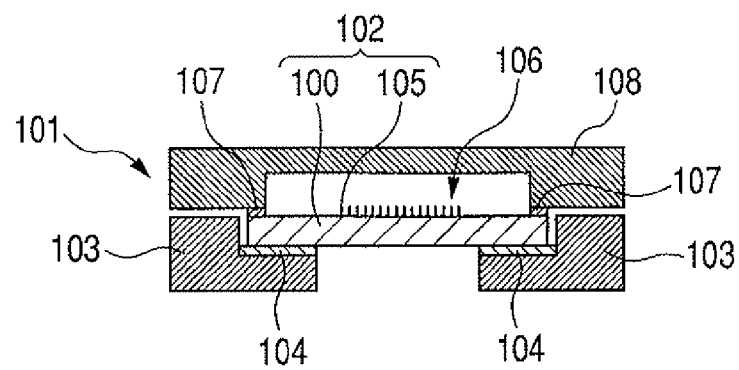
FIG. 1 is a schematic cross sectional view of the reaction space provided in the first embodiment of a biochemical reaction cassette according to the present invention, illustrating the first feasible arrangement thereof.

FIG. 1 is a schematic cross sectional view of the reaction space provided in the first embodiment of biochemical reaction cassette according to the present invention, illustrating the first feasible arrangement thereof.

Referring to FIG. 1, the biochemical reaction cassette 101 comprises a DNA micro-array 102 formed by arranging a large number of probes 105 on a substrate 100, an anchor member 103 for anchoring the DNA micro-array 102 and a ceiling member 108. The DNA micro-array 102 is tightly held to the anchor member 103 by way of an elastic member 104 typically made of rubber or a spring. The ceiling member 108 is arranged vis-à-vis the DNA micro-array 102. The ceiling member 108 is a reaction space forming member that operates as part of the reaction space 106 where a hybridization reaction is conducted. The reaction space 106 is sealed by a seal member such as an O-ring 107. The ceiling member 108 is provided with an inlet/outlet port (not shown) to be used for putting a liquid specimen that contains a target substance such as DNA into and taking it out from the inside of the biochemical reaction cassette 101. Note that a gap is shown between any two of the ceiling member 108, the DNA micro-array 102 and the anchor member 103 in each of the related figures in order to clearly show the O-ring 107, but in reality these members are tightly held in contact with each other, crushing the O-ring 107. The same members are denoted by the same respective reference numbers and will not be described repeatedly below.

Figure 2:
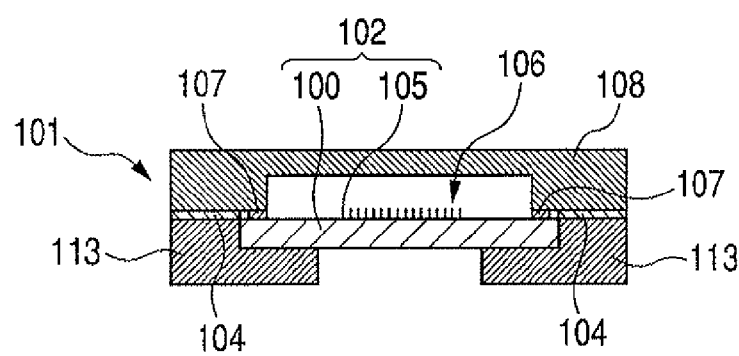
FIG. 2 is a schematic cross sectional view of the reaction space provided in the first embodiment of a biochemical reaction cassette according to the present invention, illustrating the second feasible arrangement thereof.

FIG. 2 is a schematic cross sectional view of the reaction space provided in the first embodiment of a biochemical reaction cassette according to the present invention, illustrating the second feasible arrangement thereof. Referring to FIG. 2, a DNA micro-array 102 is anchored to a substrate supporting body 113 and a ceiling member 108 is also anchored to the substrate supporting body 113 by way of an elastic member 104. In this arrangement, the ceiling member 108 also operates as the above described anchor member.

Figure 3:
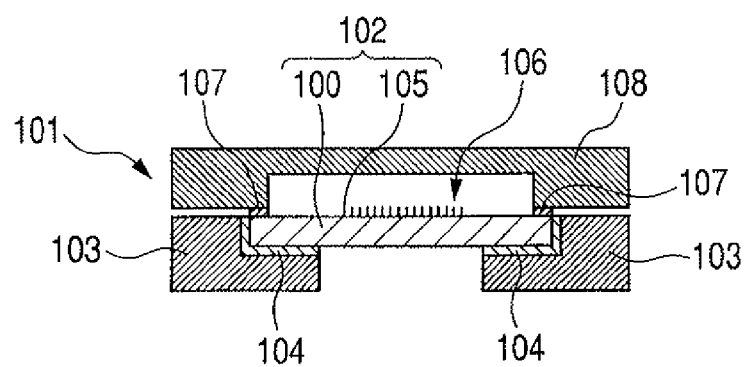
FIG. 3 is a schematic cross sectional view of the reaction space provided in the first embodiment of a biochemical reaction cassette according to the present invention, illustrating the third feasible arrangement thereof.
Figure 4:
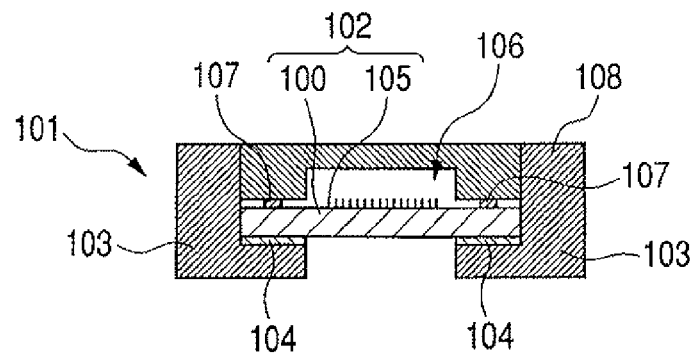
FIG. 4 is a schematic cross sectional view of the reaction space provided in the first embodiment of a biochemical reaction cassette according to the present invention, illustrating the fourth feasible arrangement thereof.

FIG. 3 is a schematic cross sectional view of the reaction space provided in the first embodiment of biochemical reaction cassette according to the present invention, illustrating the third feasible arrangement thereof. Referring to FIG. 3, the bottom surface and the lateral surface of a DNA micro-array 102 are tightly held to an anchor member 103 by way of an elastic member 104. FIG. 4 is a schematic cross sectional view of the reaction space provided in the first embodiment of a biochemical reaction cassette according to the present invention, illustrating the fourth feasible arrangement thereof. Referring to FIG. 4, the anchor member 103 of the illustrated arrangement is larger than the biochemical reaction cassette 101 anchored to it if compared with that of the first through third feasible arrangements and not only the bottom surface and the lateral surface of the DNA micro-array 102 but also the lateral surface of the ceiling member 108 are tightly held to the anchor member 103. The bottom surface of the DNA micro-array 102 is tightly held to the anchor member 103 by way of an elastic member 104.

Figure 5:
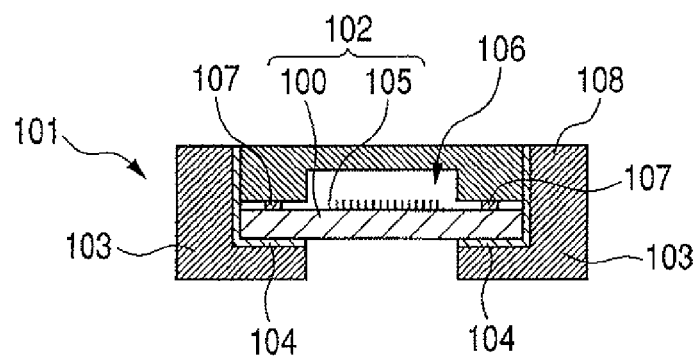
FIG. 5 is a schematic cross sectional view of the reaction space provided in the first embodiment of a biochemical reaction cassette according to the present invention, illustrating the fifth feasible arrangement thereof.

FIG. 5 is a schematic cross sectional view of the reaction space provided in a biochemical reaction cassette according to the first embodiment of the present invention, illustrating the fifth feasible arrangement thereof. Referring to FIG. 5, in the fifth feasible arrangement, the lateral surface of a DNA micro-array 102 and that of a ceiling member 108 are tightly held to an anchor member 103 by way of an elastic member 104. It should be noted here that the feasible arrangements of the first embodiment biochemical reaction cassette shown in FIGS. 1 to 5 according to the present invention are only examples and may be modified in various different ways without departing from the spirit of the present invention.

Figure 6:
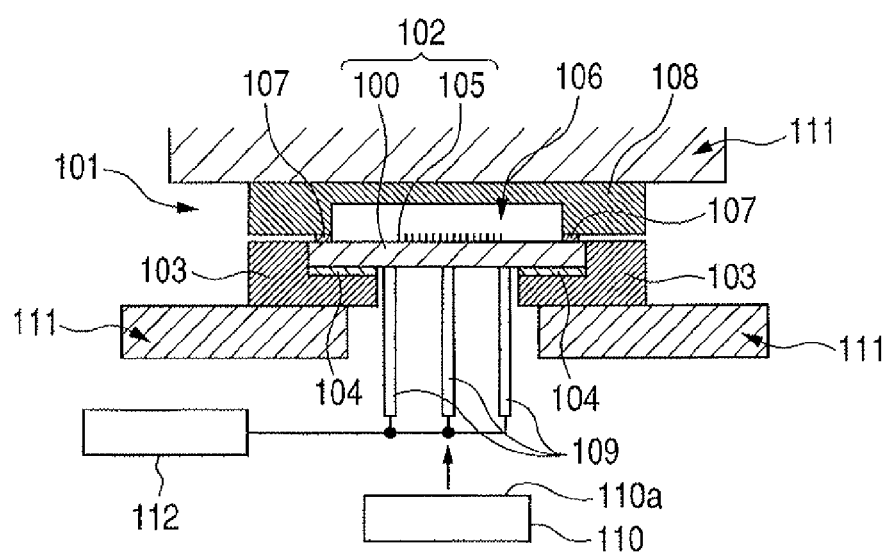
FIG. 6 is a schematic illustration of the first embodiment of a detection apparatus according to the present invention, where the first embodiment of the biochemical reaction cassette showing the first feasible arrangement is mounted.

Now, an embodiment of a detection apparatus that corresponds to the above-described biochemical reaction cassette 101 will be described below. FIG. 6 is a schematic illustration of the first embodiment of a detection apparatus according to the present invention, where the first embodiment of biochemical reaction cassette showing the first feasible arrangement is mounted. Now, the detection apparatus will be described in terms of a scene where it is used for measuring fluorescence.

Referring to FIG. 6, the detection apparatus comprises three supports 109, a drive mechanism 112 for moving the supports 109 (a mechanism for contacting the supports 109 to a substrate 100 and applying pressure thereto), a detector 110 for detecting fluorescence emitted from the probes arranged on a DNA micro-array and a holding structure 111 for holding a biochemical reaction cassette. The front ends of the above-described three supports define a plane but not located on a single straight line. The plane defined by the front end sections of the three supports is adjusted by the drive mechanism so as to run in parallel with the detection surface 110a of the detector 110. The detector 110 can detect light striking the detection surface 110a schematically illustrated in FIG. 6 in the direction indicated by the arrows and qualitatively or quantitatively reads the signals from fluorescent labels.

The drive mechanism 112 can drive the supports 109. The supports 109 can support a substrate 100 with the front ends thereof held in contact with corresponding surface of the substrate 100. In other words, the three supports 109 are pressed against the substrate 100. If the biochemical reaction cassette 101 happens to be inclined relative to the detection surface 110a, the elastic member 104 is elastically deformed so that all the front ends of the three supports 109 can be brought into contact with the substrate 100. Then, as a result, the posture of the DNA micro-array 102 is corrected so as to run in parallel with the detection surface 110a.

Figure 7:
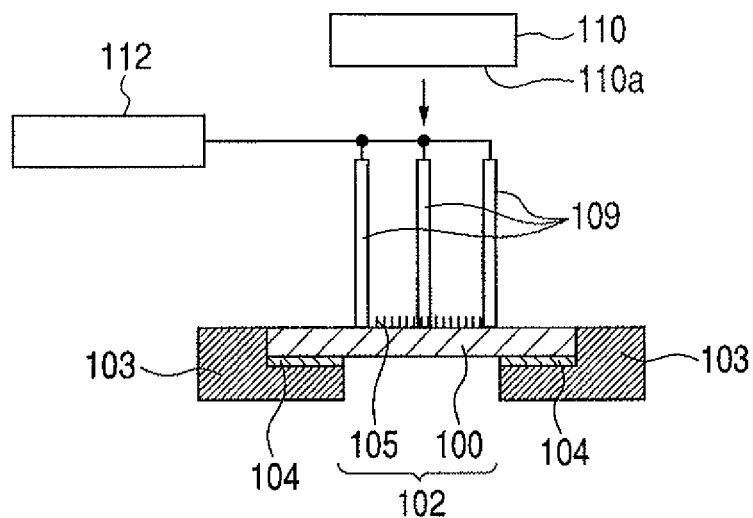
FIG. 7 is a schematic illustration of a detection apparatus according to the present invention, where the first embodiment of a biochemical reaction cassette showing the first feasible arrangement is mounted without the ceiling member thereof.

FIG. 7 is a schematic illustration of a detection apparatus according to the present invention, where only the DNA micro-array 102 and the anchor member 103 of a biochemical reaction cassette 101 of the first embodiment showing the first feasible arrangement are mounted without the ceiling member 108 thereof. With the arrangement of FIG. 7, the posture of the DNA micro-array 102 is so corrected that the plane defined by the front ends of the three supports 109 runs in parallel with the detection surface 110a of the detection apparatus. When the ceiling member 108 is removed from the biochemical reaction cassette 101 for a detecting operation, the area where the supports 109 are brought into contact can be made larger if compared with the arrangement of holding a cassette by means of a holding mechanism at the opposite surfaces thereof. In other words, the supports 109 can be pressed against the substrate 100 from the probe arranging surface side of the DNA micro-array 102 at anywhere so long as they do not contact the probes 105. Then, the detector 110 is arranged on the probe arranging surface side of the DNA micro-array 102 to detect signals such as fluorescence.

Since any conventional structure for holding the entire biochemical reaction cassette 101 may be used for this embodiment, it is not shown in FIG. 7.

2nd Embodiment

Now, the second embodiment of a biochemical reaction cassette according to the present invention will be described by referring to FIGS. 8 through 12.

Figure 8:
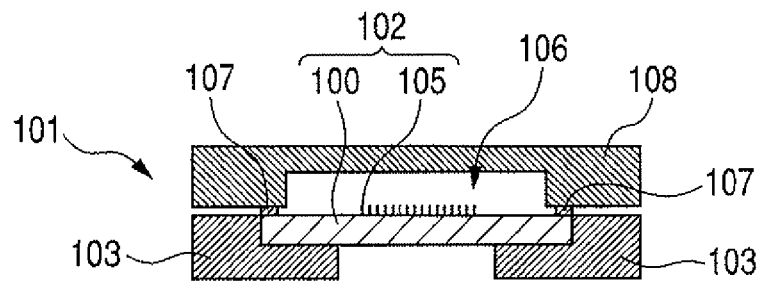
FIG. 8 is a schematic cross sectional view of the reaction space provided in the second embodiment of a biochemical reaction cassette according to the present invention, illustrating the first feasible arrangement thereof.

FIG. 8 is a schematic cross sectional view of the reaction space provided in the second embodiment of a biochemical reaction cassette according to the present invention, illustrating the first feasible arrangement thereof. As seen from FIG. 8, unlike the first embodiment that comprises an elastic member 104, the biochemical reaction cassette 101 of this embodiment does not comprise any elastic member. In other words, the micro-array 102 and the ceiling member 108 are directly secured to the anchor member 103. A reaction space is formed by the DNA micro-array 102 and the ceiling member 108 and sealed by a seal material 107 such as O-ring.

Figure 9:
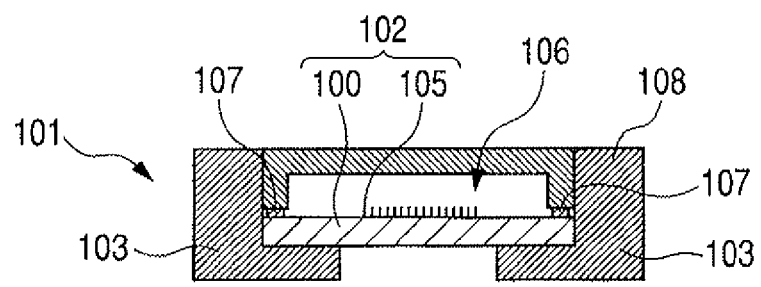
FIG. 9 is a schematic cross sectional view of the reaction space provided in the second embodiment of a biochemical reaction cassette according to the present invention, illustrating the second feasible arrangement thereof.

FIG. 9 is a schematic cross sectional view of the reaction space provided in the second embodiment of a biochemical reaction cassette according to the present invention, illustrating the second feasible arrangement thereof. Referring to FIG. 9, the anchor member 103 of the biochemical reaction cassette 101 of the illustrated arrangement is larger than that of the biochemical reaction cassette 102 of the above-described first feasible arrangement of the second embodiment and not only the bottom surface of the DNA micro-array 102 but also the lateral surface of the DNA micro-array 102 are tightly held to the anchor member 103.

Figure 10:
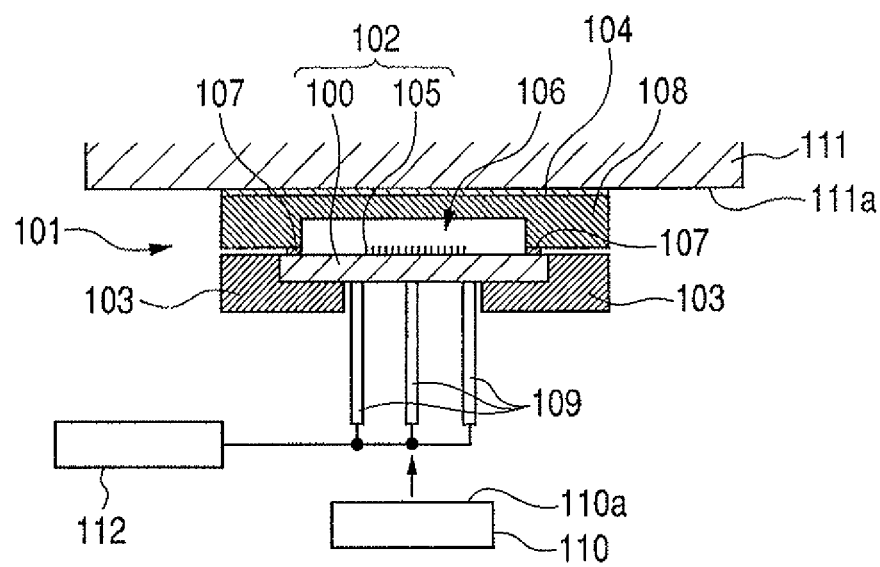
FIG. 10 is a schematic cross sectional view of the second embodiment of a detection apparatus according to the present invention and the reaction chamber of the biochemical reaction cassette mounted in it.

The detection apparatus of this embodiment is characterized by its structure. FIG. 10 is a schematic cross sectional view of the second embodiment of a detection apparatus according to the present invention and the reaction chamber of the biochemical reaction cassette mounted in it. The detection apparatus of this embodiment comprises the following components in addition to three supports 109 and a detector 110 like the detection apparatus of the first embodiment. Namely, the detection apparatus of this embodiment comprises a holding structure 111 (omitted in FIG. 7 and only partly shown in FIGS. 10 through 12), an elastic member 104 interposed between the holding structure 111 and the biochemical reaction cassette 101 and typically made of rubber or a spring. Like the first embodiment, the front ends of the three supports 109 define a plane, which is adjusted by a drive mechanism so as to run in parallel with the detection surface 110a of the detector 110.

With the detection apparatus of this embodiment, the biochemical reaction cassette 101 is fitted to the holding surface 111a of the holding structure 111 by way of the elastic member 104. Then, as in the first embodiment, the drive mechanism 112 can drive the supports 109. Thus, the supports 109 can support a substrate 100 with the front ends thereof held in contact with corresponding surface of the substrate 100. In other words, the three supports 109 are pressed against the substrate 100. If the biochemical reaction cassette 101 happens to be inclined relative to the detection surface 110a, the elastic member 104 is elastically deformed so that all the front ends of the three supports 109 can be brought into contact with the substrate 100. Then, as a result, the posture of the DNA micro-array 102 is corrected so as to run in parallel with the detection surface 110a.

Figure 11:
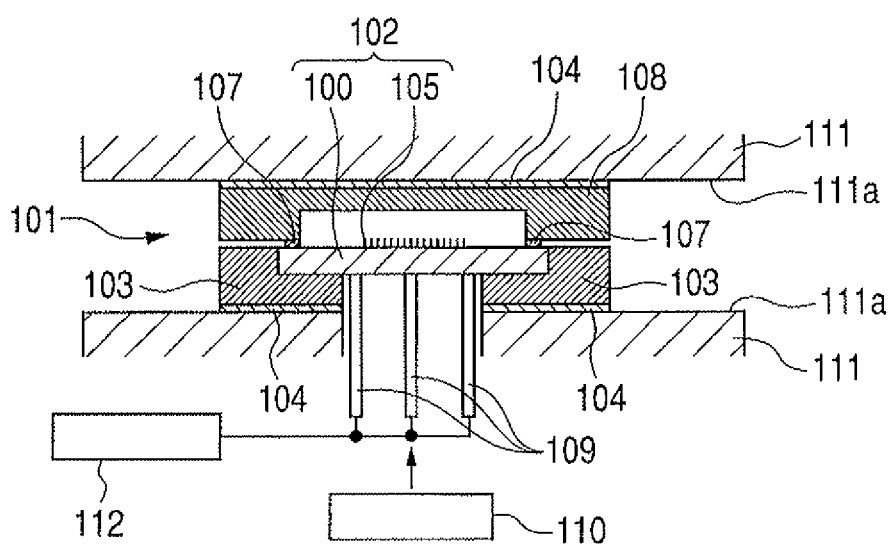
FIG. 11 is a schematic cross sectional view of a detection apparatus prepared by modifying the second embodiment of a detection apparatus according to the present invention and the reaction chamber of the biochemical reaction cassette mounted in it.

Now, a detection apparatus prepared by modifying the second embodiment of a detection apparatus will be described below. FIG. 11 is a schematic cross sectional view of a detection apparatus prepared by modifying the second embodiment of the detection apparatus according to the present invention and the reaction chamber of the biochemical reaction cassette mounted in it. The detection apparatus is provided with a holding structure 111 for holding a biochemical reaction cassette 101 by pinching it from above and from below. The holding surfaces 111a of the holding structure 111 are provided with respective elastic members. Thus, the biochemical reaction cassette 101 is rigidly held between the holding surfaces 111a of the holding structure 111 by way of the elastic members 104.

Figure 12:
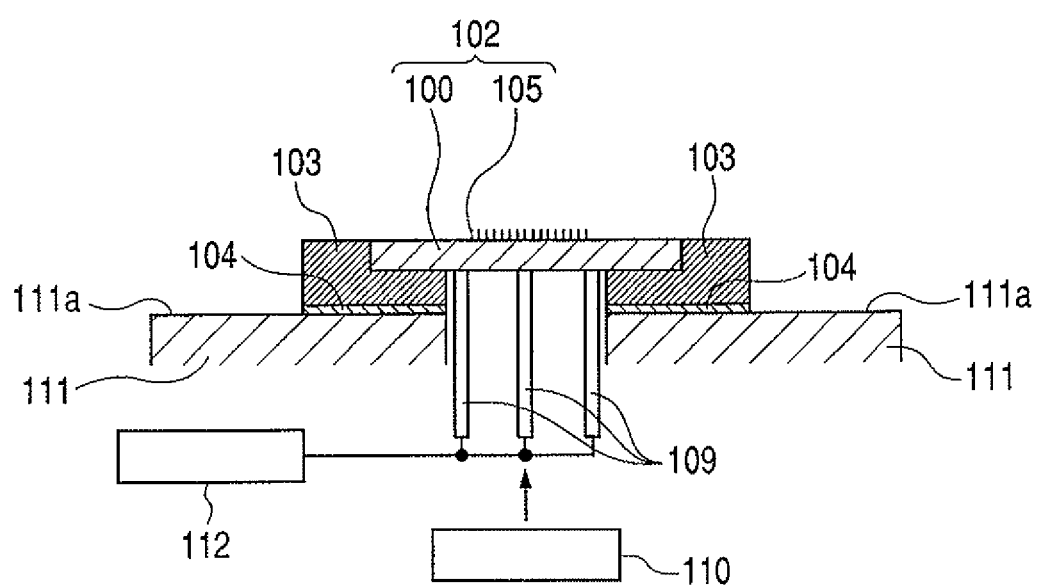
FIG. 12 is a schematic cross sectional view of a detection apparatus according to the present invention with the DNA micro-array 102 and the anchor member 103 of a biochemical reaction cassette 101 according to the present invention mounted therein without the ceiling member 108 thereof.

FIG. 12 is a schematic cross sectional view of a detection apparatus according to the present invention with the DNA micro-array 102 and the anchor member 103 of a biochemical reaction cassette 101 according to the present invention mounted therein without the ceiling member 108 thereof. The biochemical reaction cassette 101 from which the ceiling member 108 is taken off is fitted to the holding surface 111a of the holding structure 111 by way of an elastic member 104. In the modified embodiment of FIG. 12, the supports 109 and the detector 110 may be arranged at the probe arranging surface side of the DNA micro-array 102 as in the case of FIG. 7.

This embodiment is not limited to the above-described embodiment and a biochemical reaction cassette 101 showing an arrangement selected from the feasible arrangements 1 through 5 of the 1st embodiment and containing an elastic member 104 may be mounted in the detection apparatus of this embodiment for a detection process.

The number of biochemical reaction cassettes 101 to be set in a detection apparatus according to the invention and the mode of holding them are not limited to those described above. In other words, the above described embodiments may be modified in various different ways so long as the posture of the biochemical reaction cassette 101 or the DNA micro-array 102 can be corrected by the elastic deformation of the elastic member 104 when the supports 109 are pressed against the substrate 100.

Now, the present invention will be described further by way of examples.

Example 1

In Example 1, a biochemical reaction cassette containing an elastic member in the inside like the biochemical reaction cassette described above in terms of the first feasible arrangement of the 1st Embodiment was used. The steps from the step of preparing a biochemical reaction cassette according to the present invention to that of detecting a target substance by means of a detection apparatus according to the present invention and containing a biochemical reaction cassette according to the invention will sequentially be described below.

1. Preparation of DNA Micro-Array 102
(1) Cleaning of Substrate

Firstly, a synthetic quartz substrate with dimensions of 25.4 mm×76.2 mm×1 mm was brought in as the substrate 100 of the DNA micro-array 102. The substrate was put into a container and immersed in a cleansing agent for ultrasonic treatment (GPIII: tradename, available from Branson, U.S.A.) diluted by water to a 10% solution overnight. Subsequently, ultrasonic cleansing operation was conducted for 20 minutes to the substrate immersed in the cleansing agent solution and then rinsed with water to remove the cleansing agent. Moreover, the substance was rinsed with pure water and subjected to ultrasonic treatment in pure water. Next, the substance was immersed in IN aqueous sodium hydroxide heated to 80° C. in advance. Then, it was washed with water (with a low purity level) and thereafter with pure water before fed to the next step.

(2) Surface Treatment

A 1 wt % aqueous solution of N-β-(aminoethyl)-γ-aminopropyltrimethoxysilane (KBM: tradename, available from Shin-Etsu Chemical Co., Ltd.) that is a silane coupling agent having amino groups bound thereto was agitated at room temperature for 2 hours. As a result, the methoxy group in the molecule of the silane compound was hydrolyzed. Subsequently, the substrate fed from the preceding step was immersed in the solution at room temperature for an hour, washed with pure water and then dried by blowing nitrogen gas to the opposite surfaces of the substrate. Thereafter, the substrate was baked in an oven heated to 120° C. to finally introduce amino groups to the surface of the substrate. Thus, a silane coupling process was carried out in the above-described manner.

N-maleimidocaproyloxysuccinimide (EMCS: tradename, available from DOJINDO) was dissolved by 2.7 mg into a 1:1 solution of dimethylsulfoxide (DMSO) and ethanol so as to make the solution show an EMCS concentration of 0.3 mg/ml. The above-described substrate was immersed in the EMCS solution at room temperature for 2 hours. Consequently, the amino groups borne on the surface of the substrate as a result of the silane coupling process and the succinimide groups of the EMCS solution were made to react with each other. In this stage of operation, maleimide groups derived from the EMCS existed on the substrate surface. Thereafter, the substrate was drawn up from the EMCS solution and washed sequentially with a mixture solvent of DMSO and ethanol and then ethanol before it was dried by blowing nitrogen gas.

(3) Synthesis of Probe DNA (First Nucleic Acid)

A single-stranded nucleic acid of SEQ ID NO. 1 was synthesized by means of a DNA automatic synthesizer. During the synthesis process, a thiol (SH) group was introduced to the 5' terminal of the single-stranded DNA of SEQ ID NO. 1 by means of a thiol modifier (available from Glen Research Corporation, U.S.A).

(SEQ ID NO. 1)
5'HS-(CH$_2$)$_6$-O-PO2-O-ATGCATGCATGCATGCATGCATGC3'.

The DNA was de-protected and collected by means of an established method and refined by means of HPLC (high pressure liquid chromatography).

(4) DNA Ejection by Thermal Jet Printer and its Binding to Substrate

The above-described single-stranded DNA of SEQ ID NO. 1 was dissolved in a solution so as to show a concentration of 8 μM. The solution contained glycerin by 7.5 wt %, urea by 7.5 wt %, thiodiglycol by 7.5 wt % and acetylene alcohol (Acetylenol EH: tradename, available from Kawaken Fine Chemicals Co., Ltd.) by 1 wt %. In this example, only the single kind of DNA solution was spotted on the above described synthetic quartz substrate by means of an ejection spotter that includes printer heads. The printer heads were prepared by using Printer Head BC-50 (tradename) of Bubble Jet Printer BJF-850 (tradename) available from Canon and adapted to the Bubble Jet (tradename) method, which is a type of thermal jet printing method. The printer heads were remodeled so as to make each of them capable of ejecting liquid by several hundreds μl. A total of six printer heads for ejecting liquid were mounted on the ejection spotter in order to eject liquid onto the quartz substrate. Several hundreds μl of the above described DNA solution of the single kind was injected into the tank section of each of the six printer heads and the substrate that had been processed by immersing in the EMCS solution was mounted in the ejection spotter for a spotting operation. The DNA solution was ejected onto an area of 6 mm×6 mm in a central part of the substrate to form dots at a rate of 200 dpi (dots per inch (2.54 cm)), or at a pitch of 127 μm, each ejected droplet being 4 pl. Under this condition, the diameter of the spotted dots was about 50 μm. In this example, 2 rows×2 columns of matrix-shaped basic dot patterns, each being produced by ejecting the DNA solution of the single kind in 16 rows×16 columns, were formed on the substrate. After the completion of the spotting operation, the substrate was left still in a moisturizing chamber for 30 minutes to cause the maleimide groups on the substrate surface and the terminal thiol groups of the above described probe DNA to react with each other. Thereafter, the substrate was washed with pure water and stored also in pure water. Then, the substrate was cut to 1 inch×1 inch (2.54 cm×2.54 cm) pieces so as to be anchored in the biochemical reaction cassette 101.

As a result of the above-described steps (1) through (4), a DNA micro-array 102 carrying a large number of probes 105 formed on the substrate 100 was prepared.

The substrate 100 that operates as the base of the DNA micro-array 102 may alternatively be made of glass or synthetic resin. No particular limitations are posed on the probes 105 of the DNA micro-array 102 so long as they are specifically bound to the target substance. In other words, they may be nucleic acid, protein or some other substance. Any appropriate method such as an ink jet method or a pin method may be used to immobilize the probes 105 on the substrate 100.

2. Assembling of Biochemical Reaction Cassette 101

In this example, a biochemical reaction cassette 101 comprising an elastic member 104 as shown in FIG. 1 was formed. Firstly, the DNA micro-array 102 prepared in the above-described process was held to the anchor member 103 by way of a 1 mm thick piece of silicone rubber, which was the elastic member 104. Then, the ceiling member 108 was rigidly secured to the anchor member 103 to produce the reaction space 106 where the probes 105 react with the target substance by means of the DNA micro-array 102 and the ceiling member 108 and the reaction space 106 was sealed by the O-ring 107. An inlet/outlet port (not shown) to be used for putting a liquid specimen such as DNA into and taking it out of the reaction space was formed at the ceiling member 108.

3. Hybridization Reaction

A hybridization solution having the composition as shown below was injected into the biochemical reaction cassette 101 by 65 μl by way of the inlet/outlet port of the ceiling member 108 and left there at a temperature regulated to 45° C. SEQ ID NO. 2 represents a complementary nucleic acid labeled by fluorescent dye Cy3 relative to the probes 105 of SEQ ID NO. 1. A Cy3 label was introduced to the 5' terminal of SEQ ID NO. 2 by means of phosphoroamidite.

hybridization solution:
6×SSPE, 10% formamide
50 nM Cy3 label (SEQ ID NO. 2 as shown below)

(SEQ ID NO. 2)
5'Cy3-(CH$_2$)$_6$-O-PO$_2$-O-GCATGCATGCATGCATGCATGCAT3'.

The DNA was de-protected and collected by means of an established method and refined by means of HPLC (high pressure liquid chromatography).

4. Fluorescence Measurement

In this example, a fluorescence scanner having a confocal optical system was used in order to detect the desired target substance such as DNA labeled with a fluorescent label. As described earlier by referring to FIG. 6, fluorescence was measured for the substrate 100 of the DNA micro-array 102 from the side opposite to the probe arranging surface where the probes 105 are provided. Firstly, the biochemical reaction cassette was fitted to the holding structure 111. Thereafter, the three supports 109 were driven by a drive means to press the DNA micro-array 102 against the substrate 100. If the posture of the biochemical reaction cassette is not parallel to the detection surface of the fluorescence scanner, the elastic member 104 is elastically deformed as the front ends of the three supports 109 touch the substrate 100 simultaneously. Then, as a result, the posture of the DNA micro-array 102 is corrected so that the substrate 100 is held in parallel with the detection surface 110a of the detector 110. When an operation of fluorescence measurement was conducted under this condition, the degrees of luminance of all the spots on the DNA micro-array 102 were accurately observed and the dispersion of luminance was found to be 3σ/Ave<0.05.

As comparative example, a biochemical reaction cassette that was not provided with an elastic member was used for an operation of fluorescence measurement in a manner as described below. The DNA micro-array 102 was rigidly secured to the biochemical reaction cassette 101 by means of an adhesive agent without using an elastic member so that the posture of the DNA micro-array was uncontrollable. Then, the operation of fluorescence measurement was conducted without controlling the posture of the DNA micro-array by means of three supports, which characterize the present invention. As a result, the dispersion of luminance was found to be 3σ/Ave<0.2.

From the above results, it was confirmed that the dispersion of luminance of the above described example where an operation of fluorescence measurement was conducted by using a biochemical reaction cassette 101 containing an elastic member 104 and a detection apparatus according to the present invention was smaller than that of the comparative example.

Example 2

Now, Example 2 will be described below. In Example 2, a biochemical reaction cassette 101 that did not contain an elastic member 104 in the inside as described above for the second embodiment by referring to FIG. 8 was used.

1. Preparation of DNA Micro-Array 102

The DNA micro-array 102 of this example was prepared in a manner as described above for Example 1 and hence will not be described here any further.

2. Assembling of Biochemical Reaction Cassette 101

In this example, the DNA micro-array 102 prepared by way of the above-described steps and the ceiling member 108 were rigidly secured to the anchor member 103. The reaction space 106 was produced by the DNA micro-array 102 and the ceiling member 108 for the purpose of causing the probes 105 and the target substance to react with each other there and sealed by the O-ring 107. An inlet/outlet port (not shown) to be used for putting a liquid specimen such as DNA into and taking it out of the reaction space was formed at the ceiling member 108.

3. Hybridization Reaction

The hybridization reaction of this example was the same as that of Example 1 and hence will not be described here any further.

4. Fluorescence Measurement

A fluorescent scanner having a confocal optical system was used for fluorescence measurement as in Example 1. Fluorescence was measured from the side opposite to the probe arranging surface of the DNA micro-array 102 as shown in FIG. 10. Firstly, the biochemical reaction cassette 101 having a structure as described above by referring to the first feasible arrangement of the second embodiment (see FIG. 8) was fitted to the holding structure 111 by way of a 1 mm thick piece of silicone rubber, which was the elastic member 104. Thereafter, the three supports 109 were driven by a drive means to press the DNA micro-array 102 against the substrate 100. If the posture of the biochemical reaction cassette 101 is not parallel to the detection surface of the fluorescence scanner, the elastic member 104 is elastically deformed as the front ends of the three supports 109 touch the substrate 100 simultaneously. Then, as a result, the posture of the biochemical reaction cassette 101 is corrected so that the substrate 100 is held in parallel with the detection surface 110a of the detector 110. When an operation of fluorescence measurement was conducted under this condition, the degrees of luminance of all the spots on the DNA micro-array 102 were accurately observed and the dispersion of luminance was found to be 3σ/Ave<0.05. Thus, the dispersion of luminance was found much smaller than that of the above-described comparative example.

Example 3

Now, Example 3 will be described below. In Example 3, a biochemical reaction cassette 101 that did not contain an elastic member 104 in the inside as described above for the second embodiment by referring to FIG. 8 was used. The biochemical reaction cassette 101 was observed for the measurement of fluorescent after removing the ceiling member 108.

1. Preparation of DNA Micro-Array 102

The DNA micro-array 102 of this example was prepared in a manner as described above for Example 1 and hence will not be described here any further.

2. Assembling of Biochemical Reaction Cassette 101

The assembling of the biochemical reaction cassette 101 of this example was the same as that of Example 2 and hence will not be described here any further.

Hybridization Reaction

The hybridization reaction of this example was the same as that of Example 1 and hence will not be described here any further.

4. Fluorescence Measurement

A fluorescent scanner having a confocal optical system was used for fluorescence measurement as in Examples 1 and 2. Fluorescence was measured from the side opposite to the probe arranging surface of the DNA micro-array 102. However, in this example, the biochemical reaction cassette 101 was observed for the measurement of fluorescence after removing the ceiling member 108 as shown in FIG. 12.

More specifically, the ceiling member 108 was removed from the biochemical reaction cassette 101 having a structure as described above by referring to the second feasible arrangement of the second embodiment as shown in FIG. 8 to expose the probes 105 in the reaction space 106. Then, the anchor member 103 was fitted to the holding surface 111a of the holding structure 111 by way of a 1 mm thick piece of silicone rubber, which was the elastic member 104. Thereafter, the three supports 109 were driven by a drive means to be pressed against the substrate 100 of the DNA micro-array 102. If the posture of the biochemical reaction cassette 101 is not parallel to the detection surface of the fluorescence scanner, the elastic member 104 is elastically deformed as the front ends of the three supports 109 touch the substrate 100 simultaneously. Then, as a result, the posture of the DNA micro-array 102 and the anchor member 103 is corrected so that the substrate 100 is held in parallel with the detection surface 110a of the detector 110. When an operation of fluorescence measurement was conducted under this condition, the degrees of luminance of all the spots on the DNA micro-array 102 were accurately observed and the dispersion of luminance was found to be 3σ/Ave<0.05. Thus, the dispersion of luminance was found much smaller than that of the above-described comparative example.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-344368, filed Nov. 29, 2005, which is hereby incorporated by reference herein in its entirety.

What is claimed is:

1. A detection apparatus for detecting a reaction in a reaction space provided in a biochemical reaction cassette, the biochemical reaction cassette including a substrate made of glass or synthetic resin and a reaction space forming member for forming the reaction space with the substrate, the apparatus comprising:

a holding structure for holding the biochemical reaction cassette;

a detector having a detection surface for detecting the reaction in the reaction space by way of the substrate;

three or more than three supports drivably arranged between the detector and the biochemical reaction cassette, and having respective front ends to be contacted to a surface of the substrate; and a driving mechanism for driving the supports to the substrate such that the front ends of the supports are contacted to the surface of the substrate and define a plane parallel to the detection surface.

2. The detection apparatus according to claim 1, wherein the elastic member is made of a spring or rubber.

3. The detection apparatus according to claim 1, wherein the substrate carries probes immobilized thereon, the probes are specifically bindable to a target substance, and the detector is constructed to detect the target substance bound by the probes.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial
<220> FEATURE:
<223> OTHER INFORMATION: Probe for hybridization

<400> SEQUENCE: 1
atgcatgcat gcatgcatgc atgc                                    24

<210> SEQ ID NO 2
<211> LENGTH: 24
<212> TYPE: DNA
<213> ORGANISM: Artificial
<220> FEATURE:
<223> OTHER INFORMATION: Complementary sequence for probe DNA

<400> SEQUENCE: 2
gcatgcatgc atgcatgcat gcat                                    24
```